United States Patent
Zhang et al.

(10) Patent No.: US 7,125,886 B2
(45) Date of Patent: *Oct. 24, 2006

(54) 5-HT3 RECEPTOR ANTAGONISTS AND METHODS OF USE

(75) Inventors: Xiaoming Zhang, Campbell, CA (US); Jurg R. Pfister, Los Altos, CA (US); Cyrus Becker, Menlo Park, CA (US); Pascal Druzgala, Santa Rosa, CA (US)

(73) Assignee: Aryx Therapeutics, Fremont, CA (US)

( * ) Notice: Subject to any disclaimer, the term of this patent is extended or adjusted under 35 U.S.C. 154(b) by 155 days.

This patent is subject to a terminal disclaimer.

(21) Appl. No.: 10/857,108

(22) Filed: May 28, 2004

(65) Prior Publication Data

US 2004/0220246 A1    Nov. 4, 2004

Related U.S. Application Data

(63) Continuation of application No. 10/348,669, filed on Jan. 21, 2003, now Pat. No. 6,770,655.

(60) Provisional application No. 60/350,504, filed on Jan. 18, 2002.

(51) Int. Cl.
*A01N 43/42* (2006.01)
*A61K 31/44* (2006.01)
*C07D 471/00* (2006.01)
*C07D 491/00* (2006.01)
*C07D 515/00* (2006.01)

(52) U.S. Cl. .......... 514/292; 514/397; 546/86; 548/311.7

(58) Field of Classification Search .......... 546/86; 514/292, 397; 548/311.7
See application file for complete search history.

(56) References Cited

U.S. PATENT DOCUMENTS

| | | | |
|---|---|---|---|
| 5,183,820 A | * | 2/1993 | Coates et al. ............... 514/292 |
| 5,202,343 A | | 4/1993 | Coates et al. |
| 5,401,750 A | | 3/1995 | Varasi et al. |
| 6,284,770 B1 | | 9/2001 | Mangel et al. |
| 6,770,655 B1 | * | 8/2004 | Zhang et al. ............... 514/292 |

FOREIGN PATENT DOCUMENTS

| | | | |
|---|---|---|---|
| DE | 3740352 | * | 11/1987 |
| EP | 0 353 983 A2 | | 2/1990 |
| GB | 2 209 335 A | | 5/1989 |

\* cited by examiner

*Primary Examiner*—Thomas McKenzie
*Assistant Examiner*—Niloofar Rahmani
(74) *Attorney, Agent, or Firm*—McDonnell Boehnen Hulbert & Berghoff LLP

(57) ABSTRACT

The subject invention provides useful and novel 5-HT3 antagonists. The subject invention also provides methods for synthesizing the compounds of invention. The invention also provides methods for the treatment of irritable bowel syndrome and other such conditions.

12 Claims, 6 Drawing Sheets

Alosetron        Ondansetron

Granisetron

Alosetron

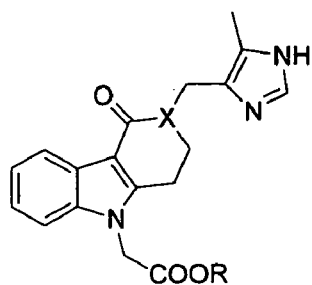
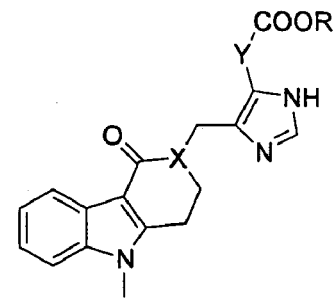
X=N, or CH
R= lower alkyl optionally substituted with OH or NH2.
X=CH, or N
Y=(CH2)n
R=lower alkyl optionally substituted with OH or NH2
Hydrolytic enzymes
Hyrolytic enzymes
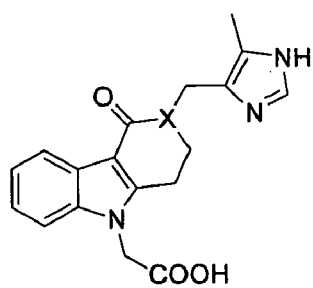
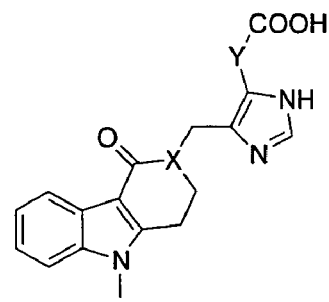
Primary inactive metabolite
X=CH, or N
Y=(CH2)n
Primary inactive metabolite
FIG. 3
FIG. 4

X=CH, or N
R=lower alkyl optionally
substituted with OH or NH2

Hyrolytic enzymes

X=CH, or N

Primary inactive metabolite

5-HT3 RECEPTOR ANTAGONISTS AND METHODS OF USE

CROSS-REFERENCE TO RELATED APPLICATION

This application is a continuation of U.S. Ser. No. 10/348,669, filed Jan. 21, 2003, now U.S. Pat. No. 6,770,655; which claims the benefit of U.S. Provisional Application Ser. No. 60/350,504, filed Jan. 18, 2002.

BACKGROUND OF INVENTION

Irritable bowel syndrome (IBS) is one of the most common gastrointestinal disorder thought to result from dysregulation of intestinal motor, sensory and CNS function. In the United States, the estimated prevalence is 15% to 20%, and 75% of patients are women. Despite its prevalence, IBS is poorly understood. It is one of over 20 functional gastrointestinal (GI) disorders that are not explained by identifiable structural or biochemical abnormalities. IBS is characterized by persistent or recurrent symptoms of abdominal pain with diarrhea and/or constipation. IBS is believed to relate to abnormalities in motility and/or afferent sensitivity as mediated by the central nervous system. Patients with IBS have a diminished quality of life and use significant health care resources.

Treatment for patients diagnosed with IBS has included antidepressant drugs, tranquilizers and laxatives. Pharmacological intervention in diarrhea-predominant IBS focuses on the reduction of bowel motility, spasms and transit times. Peripherally acting opiod ligands such as the petidine congeners diphenoxylate and loperamide and the k-opiod agonist fedotozine slow gastrointestinal transit by their effects on the circular and longitudinal muscle. While these drugs show some effects on intestinal motility, their effects on IBS-related abdominal pain and intestinal relief is generally insufficient.

Alosetron, a selective 5-HT3 receptor antagonist closely related to ondansetron in terms of chemistry and pharmacology, is the first compound of this type to be developed for irritable bowel syndrome. Alosetron and its uses are described in, for example, U.S. Pat. No. 6,284,770, which is incorporated herein by reference. A number of different 5-HT3 receptor antagonists have been disclosed, for example those of group A: indisetron, Ro-93777, YM-114, granisetron, talipexole, azasetron, tropisetron, mirtazapine, ramosetron, ondansetron, lerisetron, alosetron, N-3389, zacopride, cilansetron, E-3620, lintopride, KAE-393, itasetron, mosapride and dolasetron.

In UK Patent No. 2209335 there is disclosed, inter alia, the compound 2,3,4,5-tetrahydro-5-methyl-2-[(5-methyl-1H-imidazol-4-yl)methyl]-1H-pyrido [4,3-b]indol-1-one, now known as alosetron, and pharmaceutically acceptable salts, solvates and pharmaceutically acceptable equivalents thereof, in particular its hydrochloride salt.

5-HT3 receptor antagonists are known to be useful in the treatment of a variety of conditions involving 5-HT3 receptor-mediated mechanisms, including in particular emesis.

Ondansetron inhibits emesis by blocking 5-HT3 receptors on vagal afferent nerve terminals in the gastrointestinal mucosa and on terminals on the same vagal nerves in the vomiting system located in the dorsal medulla of brain stem. Alosetron, in various animal models, can reduce the increase in intestinal fluid secretion and motility triggered by serotonin release. Alosetron increases sensory threshold to balloon distension of the rectum, either by a direct effect on afferent pain perception, or via an increase in rectal compliance. In addition, 5-HT3 receptor antagonists have been shown to slow colonic transit in man (ondansetron and alosetron). Clinical data for up to 3 months of treatment indicate that alosetron was orally bioavailable and significantly superior to both placebo and the smooth muscle relaxant, mebeverine, in improving perception of visceral pain, spasms and diarrhea in female diarrhea-predominant IBS.

Alosetron received FDA approval for the treatment of IBS in women with diarrhea in early 2000. It is the first drug to have proven efficacy for IBS. Alosetron (Lotronex™) was launched in the US, its first market and was also launched in Puerto Rico for the treatment of women with irritable bowel syndrome who have diarrhea as the predominant symptom. However, in November 2000, Glaxo Wellcome withdrew alosetron from the US market, prompted by reports of alosetron-associated ischaemic colitis (n=49; characterized by abdominal cramping and pain) and severe constipation (n=21). The FDA also received 3 reports of deaths which were associated with alosetron.

Alosetron has approximately 60% oral bioavailability and a half-life of 1.5 hours. Greater variability was seen in the pharmacokinetic profile in all parameters in females compared with males. Females also had 60% greater drug exposure than males, with mean peak plasma concentration 45–100% higher. This is attributed to lower clearance and volume of distribution in female population. Similar gender-specific differences have been reported for ondansetron. At least 12 metabolites were detected in urine, which were eliminated from plasma with half-lives of approximately 3 hours. 6-Hydroxy-alosetron, which is twice as potent as alosetron was not detected in plasma, however the limit of detection was 6-fold higher than the Ki for this metabolite.

The pattern of fecal and urinary elimination of alosetron and its metabolites is suggestive of enterohepatic recirculation of 6-OH-alosetron, resulting in "prolonged" low level exposure. In addition, 6-OH-alosetron glucuronide and a hydroxymethyl metabolite also have potent 5-HT3 receptor binding affinity. The pharmacoynamic effects of these metabolites are unknown. Clearance was predominantly by metabolism and renal excretion. Mass balance studies with radiolabeled drug indicate that the concentration of circulating metabolite is at least 10 fold greater than that of alosetron, yet, two-thirds of the circulating radioactivity cannot be attributed to alosetron or its metabolites. This is due to slower elimination and smaller Vd of the metabolites.

Over 1200 patients with IBS received alosetron for at least 12 weeks during the Phase II and III clinical trials. Constipation was the most commonly reported adverse event, occurring in 28% of those taking alosetron and in 3% of those on placebo. This side effect appears to be dose dependent and constipation occurred more frequently in female patients. This gender difference is perhaps related to the increased drug exposure level in the female patients.

Thus, it would be particularly desirable to find potent and selective 5-HT3 antagonists having comparable pharmacodynamic effect to that of alosetron, with more predictable metabolism and an improved safety profile.

BRIEF SUMMARY

The subject invention provides useful and novel 5-HT3 antagonists and methods of use. The subject invention also provides methods for synthesizing the compounds of the subject invention. In a specific embodiment, the subject invention also provides methods for the treatment of irritable bowel syndrome.

Advantageously, the subject invention provides compounds which are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of 5-HT3 antagonist treatment.

BRIEF DESCRIPTION OF THE DRAWINGS

FIG. 3 shows specific analogs of the subject invention as well as the primary inactive metabolite after the active compound has been exposed to hydrolytic enzymes.

FIG. 4 shows specific analogs of the subject invention as well as the primary inactive metabolite after the active compound has been exposed to hydrolytic enzymes.

DETAILED DISCLOSURE

The subject invention provides novel 5-HT3 receptor antagonists. In a preferred embodiment, the 5-HT3 antatgonists of the subject invention can be deactivated to a primary inactive metabolite by hydrolytic enzymes.

Compounds of the present invention can be advantageously used to treat individuals in need of treatment with a 5-HT3 receptor antagonist. In a preferred embodiment, the compounds of the subject invention are used to treat patients suffering from gastrointestinal disorders as exemplified by irritable bowel syndrome. The compounds of the subject invention are particularly advantageous due to their predictable pharmacokinetics.

As used herein, the term "individual(s)" refers to a mammal to which is administered a compound or composition of the present invention. The mammal may be, for example a mouse, rat, pig, horse, rabbit, goat, cow, cat, dog, or human. In a preferred embodiment, the individual is a human.

Figure 1:
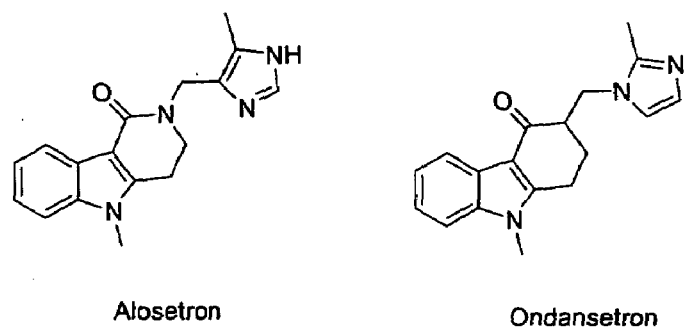
FIG. 1 shows the structures of three 5-HT3 antagonists—alosetron, ondansetron, and granisetron.
Figure 1:
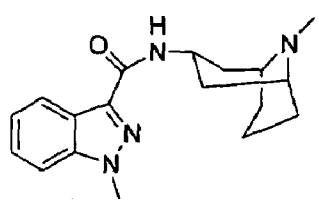

Granisetron and ondansetron are potent 5-HT3 antagonists widely used for treating emesis induced by chemotherapy (FIG. 1). While ondansetron was the first to demonstrate 5-HT3 antagonism activity in the colon, thereby reducing the sensation of pain and transit of content through the colon, alosetron was the first compound of this type to be developed for irritable bowel syndrome.

In a specific embodiment, the present invention provides novel alosetron analogs that are preferentially metabolized by endogenous hydrolytic enzymes. The novel compounds are bioactive molecules having activity on the gastrointestinal tract and undergoing deactivation to primary inactive metabolites by hydrolytic enzymes.

Figure 2:
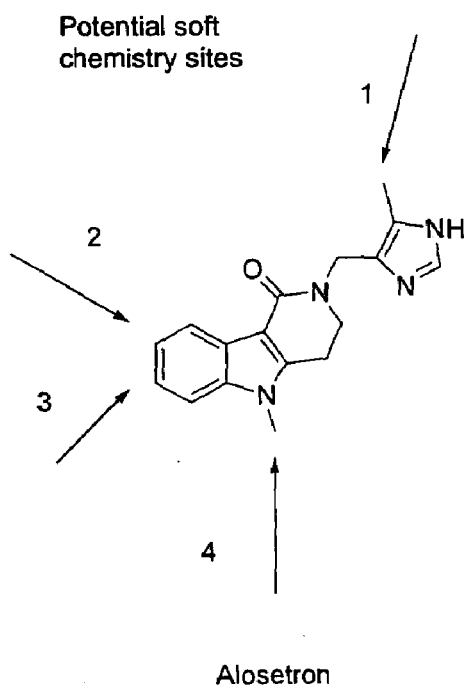
FIG. 2 shows sites at which alosetron may be modified according to the subject invention to create analogs (soft chemistry sites) which have advantageous pharmacokinetic properties as described herein.
Figure 5:
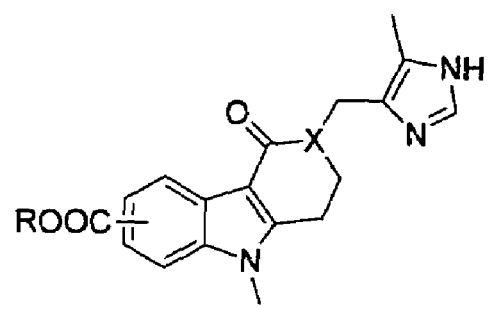
FIG. 5 shows specific analogs of the subject invention as well as the primary inactive metabolite after the active compound has been exposed to hydrolytic enzymes.
Figure 5:
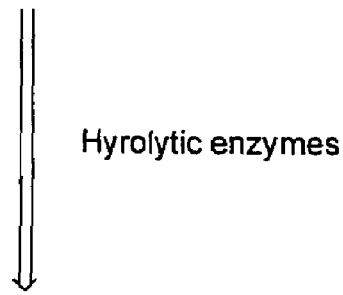
Figure 5:
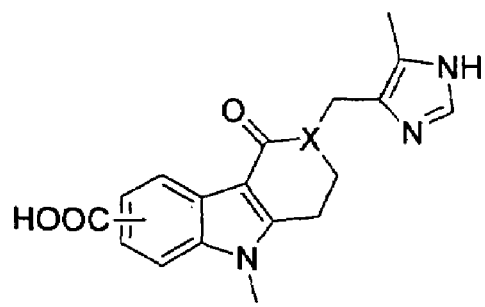

Sites at which alosetron can be modified according to the subject invention are shown in FIG. 2. Specific analogs of the subject invention, as well as the primary metabolites are shown in FIGS. 3–5.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent, metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

The compounds of this invention have one or more of the following characteristics or properties:

1. Compounds of the invention are metabolized both by CYP450 and by a non-oxidative metabolic enzyme or system of enzymes;

2. Compounds of the invention have a short (up to four (4) hours) non-oxidative metabolic half-life;

3. Oral bioavailability of the compounds is consistent with oral administration using standard pharmaceutical oral formulations; however, the compounds, and compositions thereof, can also be administered using any delivery system that produces constant and controllable blood levels over time;

4. Compounds according to the invention contain a hydrolysable bond that can be cleaved non-oxidatively by hydrolytic enzymes;

5. Compounds of the invention can be made using standard techniques of small-scale and large-scale chemical synthesis;

6. The primary metabolites of compounds of this invention result from the non-oxidative metabolism of the compounds;

7. The primary metabolites, regardless of the solubility properties of the parent drug, is, or are, soluble in water at physiological pH and have, as compared to the parent compound, a significantly reduced pharmacological activity;

8. The primary metabolites, regardless of the electrophysiological properties of the parent drug, has, or have, negligible inhibitory activity at the $IK_R$ (HERG) channel at normal therapeutic concentration of the parent drug in plasma (e.g., the concentration of the metabolite must be at least five times higher than the normal therapeutic concentration of the parent compound before activity at the $IK_R$ channel is observed);

9. Compounds of the invention, as well as the metabolites thereof, do not cause metabolic DDI when co-administered with other drugs;

10. Compounds of the invention, as well as metabolites thereof, do not elevate LFT values when administered alone.

In some embodiments, the subject invention provides compounds that have any two of the above-identified characteristics or properties. Other embodiments provide for compounds having at least any three of the above-identified properties or characteristics. In another embodiment, the compounds, and compositions thereof, have any combination of at least four of the above-identified characteristics or properties. Another embodiment provides compounds having any combination of five to ten of the above-identified characteristics or properties. In a preferred embodiment, the compounds of the invention have all ten characteristics or properties.

In various embodiments, the primary metabolites of the inventive compounds, regardless of the electrophysiological properties of the parent drug, has, or have, negligible inhibitory activity at the $IK_R$ (HERG) channel at normal therapeutic concentrations of the drug in plasma. Preferably, the concentration of the metabolite must be at least five times higher than the normal therapeutic concentration of the parent compound before activity at the $IK_R$ channel is observed. Preferably, the concentration of the metabolite must be at least ten times higher than the normal therapeutic concentration of the parent compound before activity at the $IK_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, and other bonds that can be cleaved by hydrolases.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. The accompanying figures show certain specific compounds including those substituted with lower ($C_{1-4}$) alkyl. The person skilled in the art having the benefit of the instant disclosure would appreciate that other substituents could be made in order to arrive at other compounds having the advantageous biological activity (5-HT3 receptor antagonist) and pharmacokinotic properties.

As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

The subject invention further pertains to enantiomerically isolated compounds, and compositions comprising the compounds, for 5-HT3 antagonism. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

A further aspect of the subject invention pertains to the breakdown products which are produced when the therapeutic compounds of the subject invention are acted upon by hydrolytic enzymes, such as esterases. The presence of these breakdown products in urine or serum can be used to monitor the rate of clearance of the therapeutic compound from a patient.

The compounds of this invention have therapeutic properties similar to those of the unmodified parent compounds. Accordingly, dosage rates and routes of administration of the disclosed compounds are similar to those already used in the art and known to the skilled artisan (see, for example, *Physicians' Desk Reference*, 54$^{th}$ Ed., Medical Economics Company, Montvale, N.J., 2000).

The compounds of the subject invention can be formulated according to known methods for preparing pharmaceutically useful composition. Formulations are described in detail in a number of sources, which are well known and readily available to those skilled in the art. For example, *Remington's Pharmaceutical Science* by E. W. Martin describes formulation, which can be used in connection with the subject invention. In general, the compositions of the subject invention are formulated such that an effective amount of the bioactive compound(s) composition.

In accordance with the subject invention, pharmaceutical compositions are provided which comprise, as an active ingredient, an effective amount of one or more of the compounds and one or more non-toxic, pharmaceutically acceptable carriers or diluents. Examples of such carriers for use in the invention include ethanol, dimethyl sulfoxide, glycerol, silica, alumina, starch, and equivalent carriers and diluents. Further, acceptable carriers can be either solid or liquid. Solid form preparations include powders, tablets, pills, capsules, cachets, suppositories and dispersible granules. A solid carrier can be one or more substances, which may act as diluents, flavoring agents, solubilizers, lubricants, suspending agents, binders, preservatives, tablet disintegrating agents or encapsulating materials.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenges.

Figure 6:
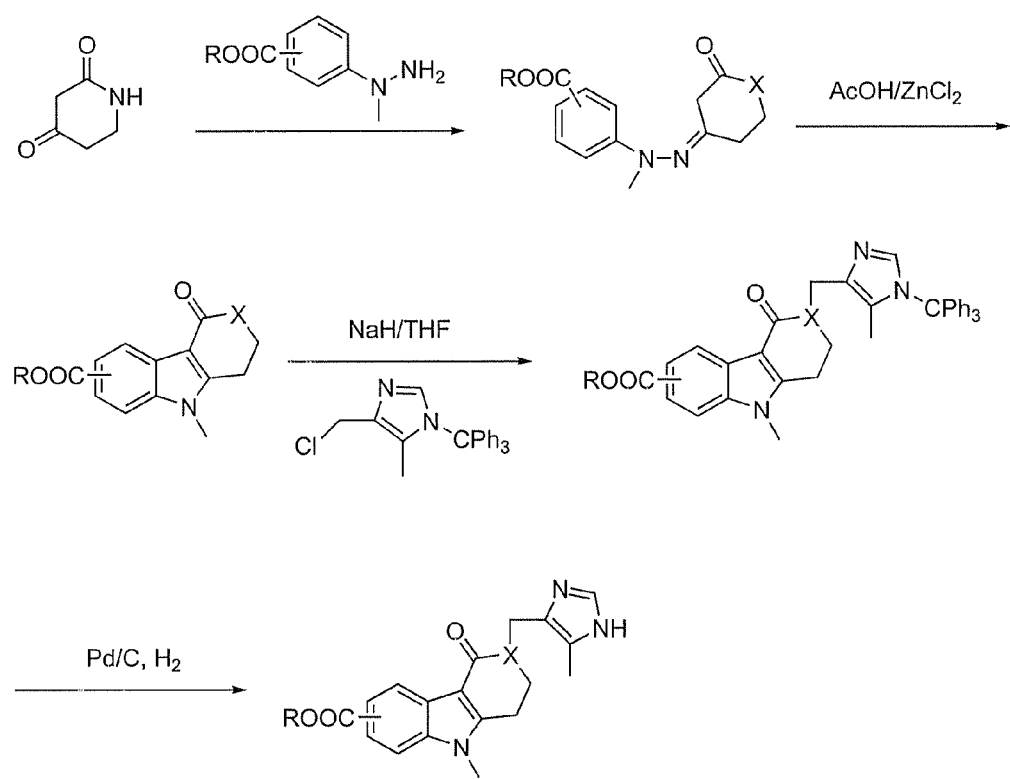
FIG. 6 shows an example of a synthetic scheme which can be used to synthesize certain specific analogs of the subject invention.
Figure 7:
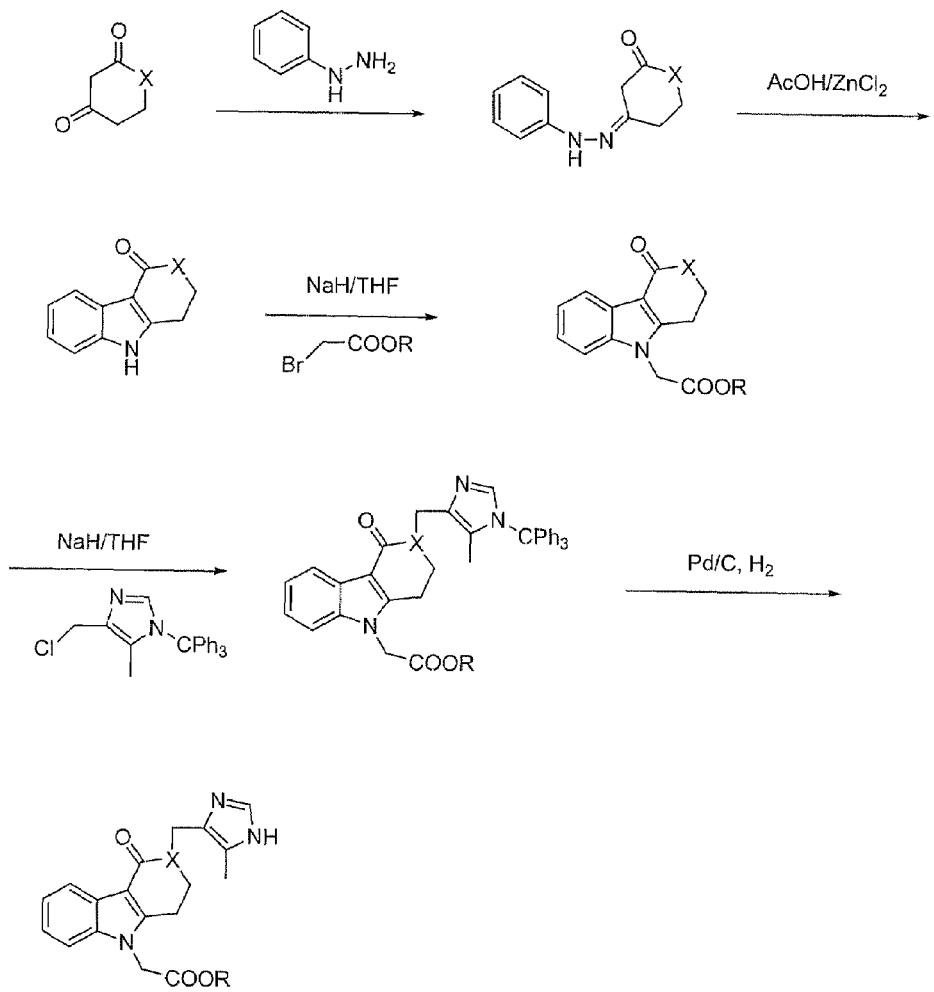
FIG. 7 shows an example of a synthetic scheme which can be used to synthesize certain specific analogs of the subject invention.
Figure 8:
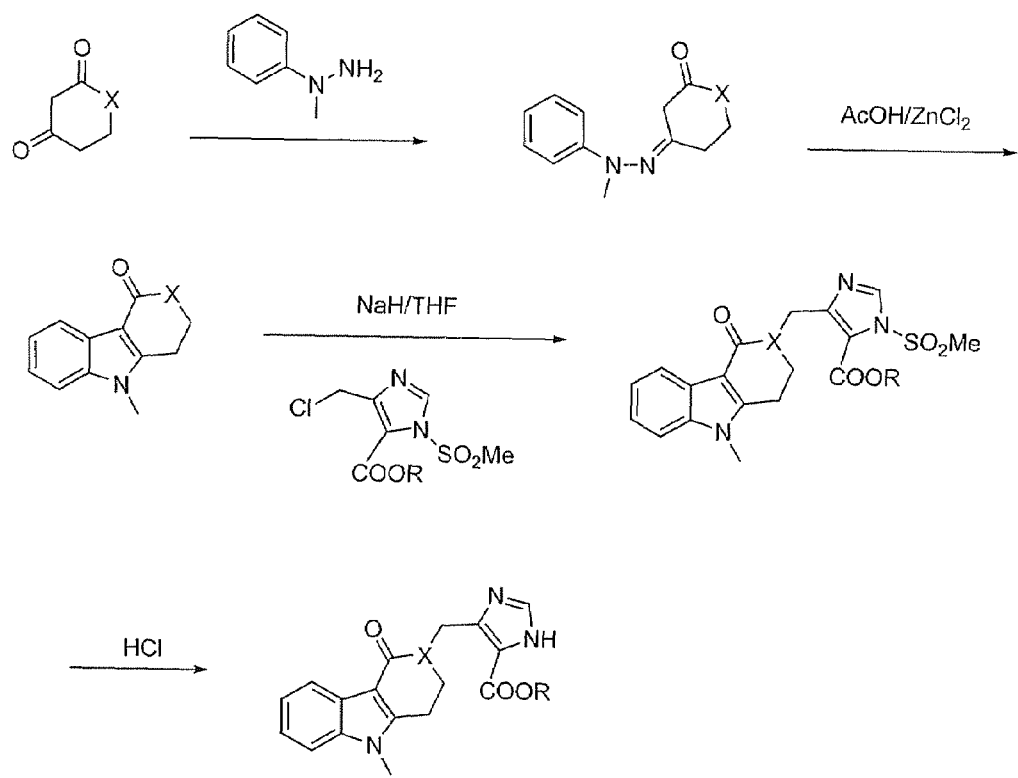
FIG. 8 shows an example of a synthetic scheme which can be used to synthesize certain specific analogs of the subject invention.

The subject invention further provides methods of synthesizing the unique and advantageous therapeutic compounds of the subject invention. Particularly, methods of producing less toxic therapeutic agents comprising introducing ester groups into therapeutic agents are taught. The ester linkage may be introduced into the compound at a site which is convenient in the manufacturing process for the compounds of the invention. Various exemplary synthetic routes for the preparation of the compounds of the subject invention are described in FIGS. 6–8. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. The compound, wherein said compound has the following structure, or a salt of a compound having the following structure:

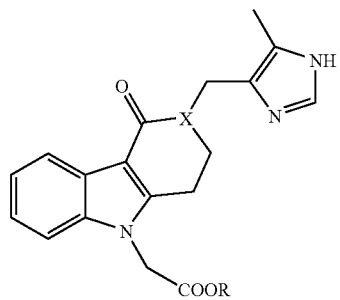

wherein,
X=N or CH; and
R=lower alkyl substituted with OH or $NH_2$.

2. The compound, according to claim 1, having the following formula:

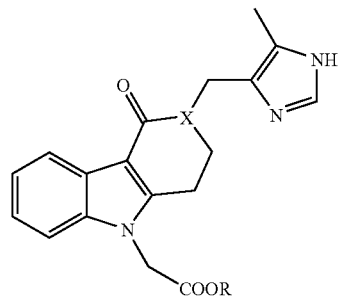

wherein
X=N or CH; and
R=lower alkyl substituted with OH or $NH_2$.

3. The compound, according to claim 1, wherein said compound has the following structure, or a salt of a compound having the following structure:

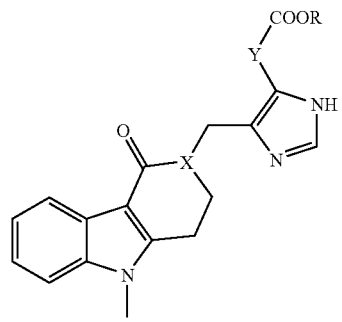

wherein
X=N or CH;
Y=$(CH_2)_n$;
n is 0; and
R=lower alkyl optionally substituted with OH or $NH_2$.

4. The compound, according to claim 3, having the following structure:

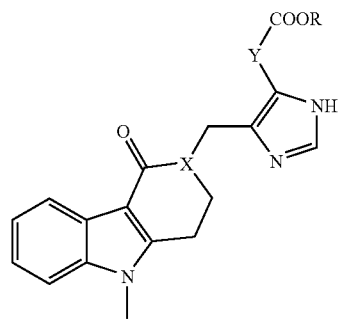

wherein
X=N or CH;
Y=$(CH_2)_n$;
n is 0; and
R=lower alkyl optionally substituted with OH or $NH_2$.

5. The compound, according to claim 1, wherein said compound has the following structure, or a salt of a compound having the following structure:

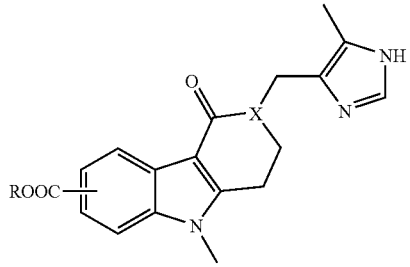

wherein
X=N or CH; and
R=lower alkyl optionally substituted with OH or NH$_2$.

6. The compound, according to claim 5, having the following structure:

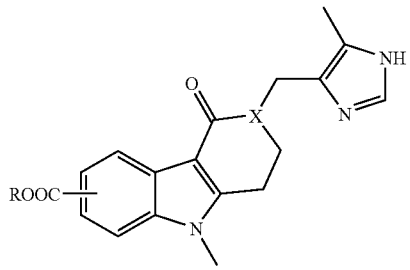

wherein
X=N or CH; and
R=lower alkyl optionally substituted with OH or NH$_2$.

7. The pharmaceutical composition, comprising a compound, or salt thereof, wherein said compound has the following structure:

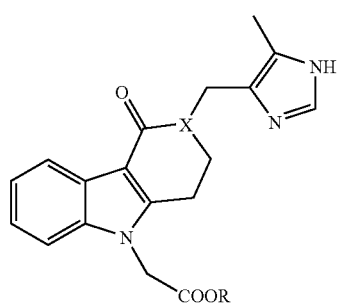

wherein
X=N or CH; and
R=lower alkyl substituted with OH or NH$_2$.

8. The composition, according to claim 7, comprising a compound having the following structure:

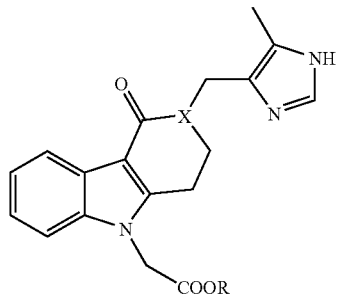

wherein
X=N or CH; and
R=lower alkyl substituted with OH or NH$_2$.

9. The composition, according to claim 7, comprising a compound or salt thereof, wherein said compound has the following structure:

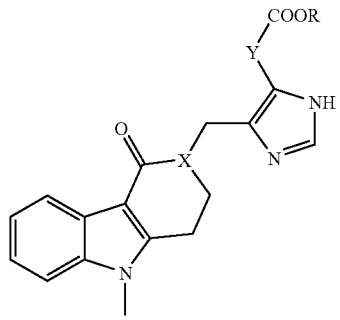

wherein
X=N or CH;
Y=(CH$_2$)$_n$;
n is 0; and
R=lower alkyl optionally substituted with OH or NH$_2$.

10. The composition, according to claim 7, comprising a compound having the following structure:

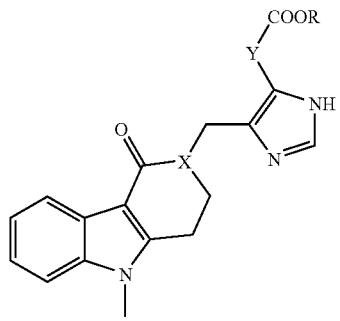

wherein
X=N or CH;
Y=(CH$_2$)$_n$;
n is 0; and
R=lower alkyl optionally substituted with OH or NH$_2$.

11. The composition, according to claim 1, comprising a compound, or salt thereof, wherein said compound has having the following structure:

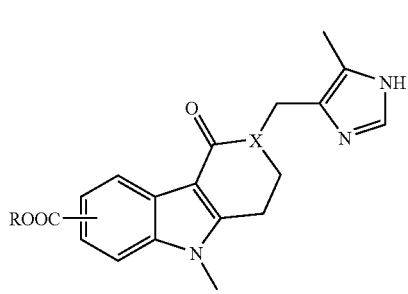

wherein
X=N or CH; and
R=lower alkyl optionally substituted with OH or NH₂.

12. The composition, according to claim 11, comprising a compound having the following structure:

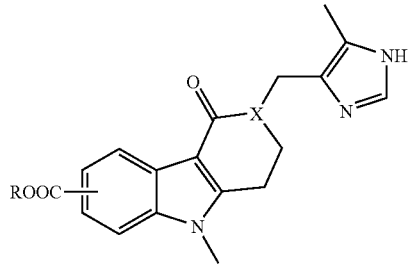

wherein
X=N or CH; and
R=lower alkyl optionally substituted with OH or NH₂.

* * * * *